(12) United States Patent
Kellerman et al.

(10) Patent No.: US 11,786,299 B2
(45) Date of Patent: *Oct. 17, 2023

(54) SINGLE CATHETER ELECTRODE TISSUE CUTTING SYSTEM FOR CREATING ANASTOMOSES

(71) Applicant: Avenu Medical, Inc., San Juan Capistrano, CA (US)

(72) Inventors: Brad M. Kellerman, Escondido, CA (US); Justin K. Mann, Lake Elsinore, CA (US)

(73) Assignee: AVENU MEDICAL, INC.

( * ) Notice: Subject to any disclaimer, the term of this patent is extended or adjusted under 35 U.S.C. 154(b) by 339 days.

This patent is subject to a terminal disclaimer.

(21) Appl. No.: 17/008,412

(22) Filed: Aug. 31, 2020

(65) Prior Publication Data

US 2020/0397438 A1    Dec. 24, 2020

Related U.S. Application Data

(63) Continuation of application No. 15/982,946, filed on May 17, 2018.

(Continued)

(51) Int. Cl.
*A61B 18/14* (2006.01)
*A61M 25/00* (2006.01)
(Continued)

(52) U.S. Cl.
CPC .. *A61B 18/1492* (2013.01); *A61B 17/320068* (2013.01); *A61B 18/082* (2013.01);
(Continued)

(58) Field of Classification Search
CPC .. A61B 2017/00867; A61B 2017/1107; A61B 2017/1121; A61B 2017/1132;
(Continued)

(56) References Cited

U.S. PATENT DOCUMENTS 6,712,817 B1   3/2004   Goto
8,951,276 B2   2/2015   Kellerman et al.
(Continued)

FOREIGN PATENT DOCUMENTS

JP    11-19091 A    1/1999
WO    9732532 A1    9/1997
(Continued)

OTHER PUBLICATIONS

Non-Final Office action from corresponding U.S. Appl. No. 15/982,946, dated Dec. 23, 2021, 23 pages.
(Continued)

*Primary Examiner* — Ronald Hupczey, Jr.
*Assistant Examiner* — Bradford C. Blaise
(74) *Attorney, Agent, or Firm* — Stinson LLP

(57) ABSTRACT

A catheter and tissue cutting system percutaneously permits the creation of an anastomosis between a first and second anatomical structure, such as a vein and an artery. The system comprises a catheter having a main body with a lumen and tapered distal tip, configured to be moved distally into the first anatomical structure over a primary guidewire. A cutting electrode is nested in the main body, with a lumen which tracks over a secondary guidewire, and is insertable into the secondary anatomical structure. An energy supply is operative to energize the cutting electrode in order to cut a tissue wall defining the first anatomical structure.

15 Claims, 12 Drawing Sheets

Related U.S. Application Data

(60) Provisional application No. 62/507,362, filed on May 17, 2017.

(51) Int. Cl.

| | | |
|---|---|---|
| *A61M 25/01* | (2006.01) | |
| *A61M 25/06* | (2006.01) | |
| *A61B 17/32* | (2006.01) | |
| *A61B 18/08* | (2006.01) | |
| *A61B 17/11* | (2006.01) | |
| *A61B 18/00* | (2006.01) | |
| *A61M 25/09* | (2006.01) | |
| *A61M 29/00* | (2006.01) | |
| *A61B 90/00* | (2016.01) | |
| *A61B 17/00* | (2006.01) | |

(52) U.S. Cl.
CPC ......... *A61B 18/14* (2013.01); *A61M 25/0068* (2013.01); *A61M 25/0082* (2013.01); *A61M 25/0105* (2013.01); *A61M 25/0108* (2013.01); *A61M 25/065* (2013.01); *A61B 17/11* (2013.01); *A61B 2017/00867* (2013.01); *A61B 2017/1107* (2013.01); *A61B 2017/1139* (2013.01); *A61B 2018/00345* (2013.01); *A61B 2018/00404* (2013.01); *A61B 2018/00601* (2013.01); *A61B 2018/144* (2013.01); *A61B 2018/1475* (2013.01); *A61B 2090/3966* (2016.02); *A61M 25/09* (2013.01); *A61M 29/00* (2013.01); *A61M 2025/0166* (2013.01); *A61M 2205/32* (2013.01); *A61M 2205/3331* (2013.01); *A61M 2210/12* (2013.01)

(58) Field of Classification Search
CPC .... A61B 2017/1135; A61B 2017/1139; A61B 17/11; A61B 17/320068; A61B 2018/00345; A61B 2018/00351; A61B 2018/00386; A61B 2018/00404; A61B 2018/00601; A61B 2018/1405; A61B 2018/144; A61B 2018/1475; A61B 2018/1492; A61B 18/082; A61B 18/14; A61B 90/39; A61B 2090/3966; A61M 25/0067; A61M 25/0068; A61M 25/0082; A61M 25/0105; A61M 25/0108; A61M 25/065; A61M 25/09; A61M 2025/0166; A61M 29/00

See application file for complete search history.

(56) References Cited

U.S. PATENT DOCUMENTS

| | | |
|---|---|---|
| 9,138,230 B1 | 9/2015 | Buelna |
| 9,439,710 B2 | 9/2016 | Reu et al. |
| 9,445,868 B2 | 9/2016 | Hull et al. |
| 9,452,015 B2 | 9/2016 | Kellerman et al. |
| 9,474,562 B2 | 10/2016 | Kellerman et al. |
| 2006/0111704 A1 | 5/2006 | Brenneman |
| 2010/0268316 A1 | 10/2010 | Brenneman et al. |
| 2011/0306959 A1* | 12/2011 | Kellerman ............ A61B 17/11 606/28 |
| 2011/0306993 A1 | 12/2011 | Hull |
| 2014/0107642 A1* | 4/2014 | Rios ............... A61B 17/320016 606/41 |
| 2015/0105714 A1 | 4/2015 | Laudenslager et al. |
| 2016/0101283 A1 | 4/2016 | Sharma |
| 2016/0135873 A1 | 5/2016 | Hull et al. |
| 2017/0087294 A1 | 3/2017 | Hull et al. |
| 2017/0105797 A1* | 4/2017 | Mikkaichi .......... A61B 1/00087 |
| 2018/0333203 A1* | 11/2018 | Kellerman ........ A61M 25/0108 |
| 2019/0069949 A1 | 3/2019 | Vrba et al. |
| 2020/0397438 A1 | 12/2020 | Kellerman et al. |

FOREIGN PATENT DOCUMENTS

| | | |
|---|---|---|
| WO | 2011159802 A1 | 12/2011 |
| WO | 2014130850 A1 | 8/2014 |
| WO | 2016145202 A1 | 9/2016 |

OTHER PUBLICATIONS

International Search Report and Written Opinion dated Sep. 11, 2018 for corresponding PCT App. No PCT/US2018/033259.
Office Action dated Oct. 20, 2020 in connection with corresponding Japanese App. No. 2019-559313.
Extended European Search Report dated Jan. 12, 2021 in connection with European App. No. 18803291.6.
Australian Examination Report No. 1 for Standard Patent Application No. 2018269737, dated Apr. 24, 2023, 5 pages.

* cited by examiner

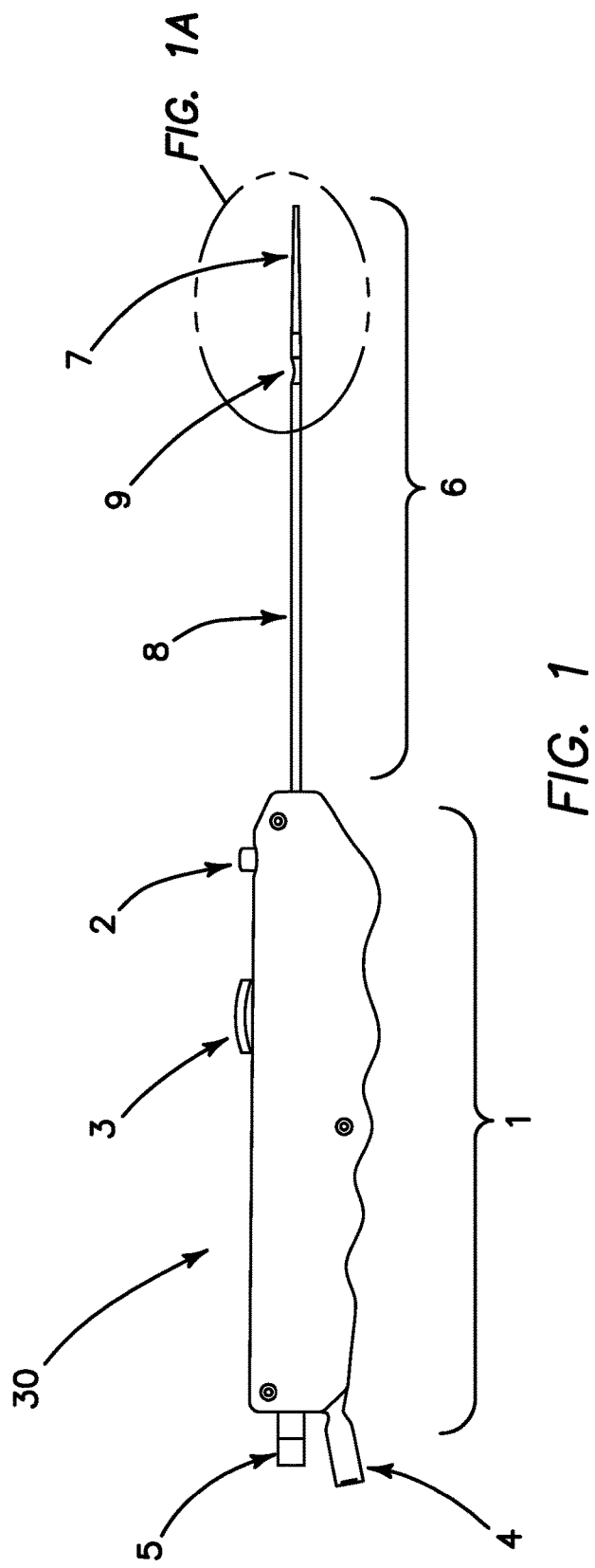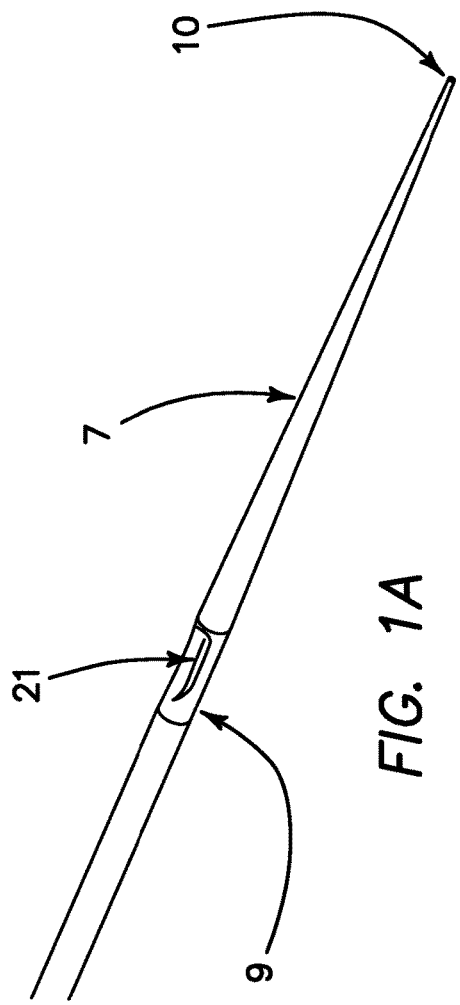
FIG. 1
FIG. 1A
FIG. 2

SINGLE CATHETER ELECTRODE TISSUE CUTTING SYSTEM FOR CREATING ANASTOMOSES

This application is a continuation under 35 U.S.C. 120 of U.S. patent application Ser. No. 15/982,946, entitled Single Catheter Electrode Tissue Cutting System for Creating Anastomoses, filed on May 17, 2018, which in turn claims the benefit under 35 U.S.C. 119(e) of the filing date of Provisional U.S. Application Ser. No. 62/507,362, entitled Single Catheter Electrode Tissue Cutting System for Creating Anastomoses, filed on May 17, 2017, which applications are each expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with (1) catheters placed in large veins, (2) prosthetic grafts attached to an artery and a vein, or (3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater, in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialyzed and non-dialyzed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present invention provides a catheter and tissue cutting system for percutaneously creating an anastomosis between a first and second anatomical structure. The system comprises a catheter having a main body with a lumen and tapered distal tip, configured to be moved distally into the first anatomical structure over a primary guidewire. A cutting electrode is nested in the main body, with a lumen which tracks over a secondary guidewire, and is insertable into the secondary anatomical structure. An energy supply is operative to energize the cutting electrode in order to cut a tissue wall defining the first anatomical structure. In exemplary methods of use, the first and second anatomical structures comprise adjacent blood vessels, such as a vein and an artery.

The system described above further comprises a coaxial piercing member having an inner lumen, the coaxial piercing member being configured to be moved distally relative to the main body and to pierce through the wall of the first anatomical structure into the second anatomical structure. A primary guidewire is provided, which is advanced distally in the first anatomical structure, and a secondary guidewire is placed through the inner lumen of the piercing element for forming a guide rail into the patient, through the first anatomical structure, and into the second anatomical structure. The piercing member is retractable into the main body lumen. The primary guidewire extends through and distally from the main body lumen, over which the catheter main body is tracked distally into the first anatomical structure. The secondary guidewire, from the first anatomical structure into the secondary anatomical structure, extends through and distally from the cutting electrode, over which the cutting electrode separates from the main body into the adjacent anatomical structure. The cutting electrode is resiliently biased, such as by spring loading, and applies compression between the walls of the anatomical structures when it is advanced into the secondary anatomical structure. The cutting electrode is extendable from and retractable into the main body through a side port in the main body, in illustrated embodiments.

The cutting electrode may be comprised of one of stainless steel, Nitinol, or Nichrome. The energy supply may supply RF, ultrasonic, or resistive heating energy to the cutting electrode. In some embodiments, the piercing member comprises a micropuncture needle. In some embodiments, the cutting electrode comprises a cutter wire. In illustrated methods, the primary anatomical structure is a vein and the secondary anatomical structure is an artery. The cutter wire may comprise a polyamide insulation and the cutting electrode may be disposed at a distal end of the polyamide insulation portion.

A positioning feature may be disposed on the main body which is configured to detect when the electrode has entered the secondary anatomical structure. The positioning feature may comprise one of a pressure sensor, radiopaque marker, or a bleed port.

In another aspect of the invention, there is provided a catheter and tissue cutting system for creating intravascular access and guidewire placement. This system comprises a piercing member configured to be moved distally and to pierce through tissue while being distally moved, a catheter comprising a main body having a lumen, configured to be moved distally into a blood vessel through an aperture created by the piercing member, and a cutting electrode disposable in said main body lumen, and insertable distally through the main body lumen into the blood vessel or a closely adjacent blood vessel. An actuator is operable to extend and retract the cutting electrode. An energy supply is operative to energize the cutting electrode in order to cut a tissue wall defining the blood vessel.

A first guidewire extends through and distally from the main body lumen, over which the catheter main body is tracked distally into the blood vessel. A second guidewire extends through and distally from the cutting electrode, over which the cutting electrode extends distally from the main body. The cutting electrode is resiliently biased, such as by spring-loading, toward and fully retractable into the main body. The cutting electrode is extendable from and retractable into the main body through a side port in the main body.

The cutting electrode may be comprised of one of stainless steel, Nitinol, or Nichrome. The energy supply supplies RF, ultrasonic, or resistive heating energy to the cutting electrode. The piercing member may comprise, in some embodiments, a micropuncture needle. The cutting electrode may comprise a cutter wire, which, in some embodiments, may comprise a polyamide insulation, with the cutting electrode being disposed at a distal end of the polyamide insulation portion.

A positioning feature may be provided on the main body which is configured to detect when the main body has entered the blood vessel. The positioning feature may comprise one of a pressure sensor, radiopaque marker, or a bleed port.

In still another aspect of the invention, there is disclosed a method of creating intravascular access, wherein the method comprises a step of positioning the main body of a device over a guidewire within a first anatomical structure, extending a cutter electrode from the main body over a secondary guidewire into a second adjacent anatomical structure, through adjacent walls defining each of the first anatomical structure and the second anatomical structure, and retracting the secondary guidewire, thereby allowing the cutting electrode to compress the adjacent walls together. The cutter electrode is then energized, followed by a step of cutting through the adjacent walls to form an access aperture between the first and second anatomical structures.

The method may further comprise a step of nesting the cutter electrode into the main body. During the step of advancing the catheter over the secondary guidewire the cutting electrode is deployed from the main body and into the secondary anatomical structure. Then, the method further comprises a step of withdrawing the main body from the procedural site after the aperture is created.

The tapered distal tip of the catheter allows it to be inserted through the skin and into the primary anatomical structure without a sheath.

A further inventive step comprises using a needle to gain access to the first and second blood vessels percutaneously before the positioning step. The needle is tracked over a guidewire. The needle is withdrawn before the positioning step.

Before the extending step, a second electrode guidewire is placed into one of the blood vessels, through a lumen in the cutter electrode.

In yet another aspect of the invention, there is disclosed a method of creating intravascular access, which comprises steps of positioning the main body of a device within a first blood vessel, extending a cutter electrode from the main body into a second adjacent blood vessel, through adjacent walls defining each of the first blood vessel and the second blood vessel, retracting the cutter electrode and compressing the adjacent walls together, energizing the cutter electrode, and cutting through the adjacent walls to form an access aperture between the first and second blood vessels.

The method further comprises a step of retracting the cutter electrode into the main body, after which the main body is withdrawn from the procedural site. The needle may be used to gain access to the first and second blood vessels percutaneously before the positioning step. The needle is tracked over a guidewire, and is subsequently withdrawn before the positioning step. Before the extending step, a second electrode guidewire is placed into one of the blood vessels, through a lumen in the cutter electrode.

BRIEF DESCRIPTION OF THE DRAWINGS

FIG. 1 is a schematic side view of one embodiment of a device constructed in accordance with the principles of the invention;

FIG. 1a is an enlarged isometric view of the distal end of the device shown in FIG. 1;

DETAILED DESCRIPTION OF THE INVENTION

Figure 2:
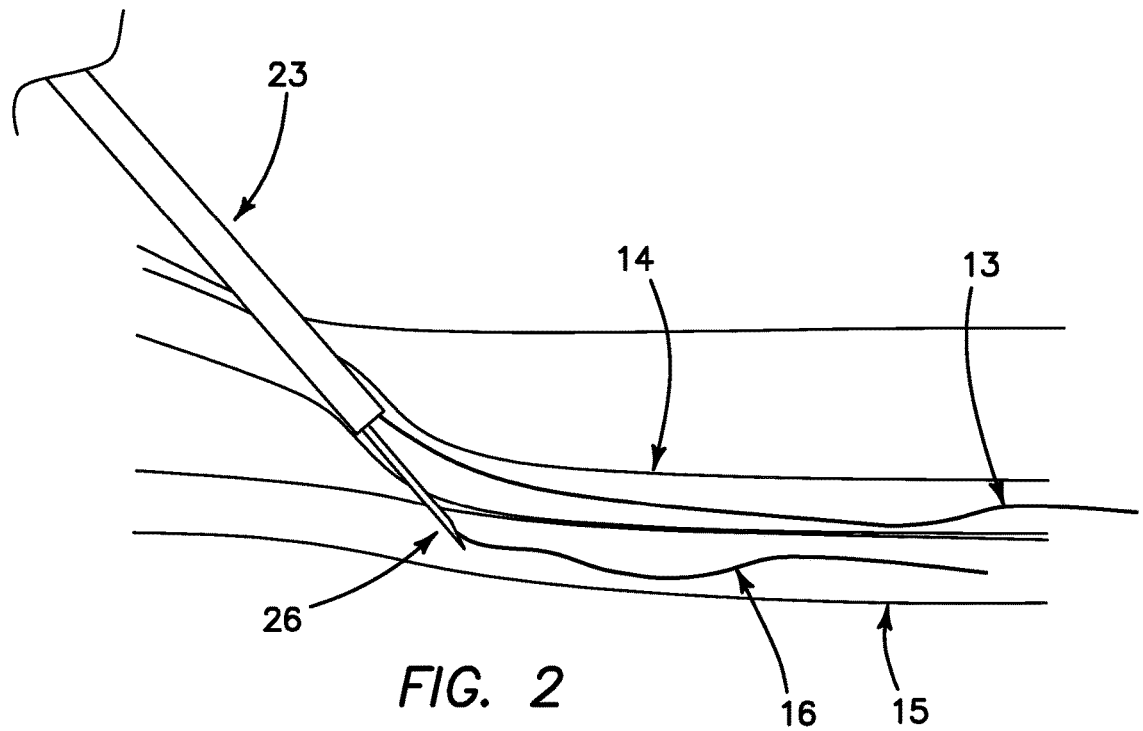
FIG. 2 is a view of one exemplary embodiment of a resiliently biased "fixed" electrode embodiment of the present invention, wherein a needle has been utilized to puncture from a first vessel into an adjacent vessel.

FIG. 1 is a schematic view illustrating a device constructed in accordance with an exemplary embodiment of the present invention. The device 30 comprises a handle 1, on which is a first actuator 2 (illustrated as a button) and a second actuator 3 (illustrated as a thumb tab). Also disposed on the handle 1 is a main body lumen Luer 4 and an electrode lumen Luer 5. A catheter 6 extends distally from the handle 5. The catheter 6 comprises a dilator tip 7, a catheter shaft 8, and a main body 9.

FIG. 1a is an enlarged isometric view of the dilator tip 7 of the catheter 6 denoted by an oval A in FIG. 1. The dilator tip 7 comprises a main body lumen terminus 10, as well as a resiliently biased cutting electrode 21. This resilient bias may be accomplished by spring-loading the electrode.

FIG. 2 is a view of one exemplary embodiment of a spring loaded "fixed" electrode embodiment of the device of the present invention. A sheath 23 and a venous guidewire 13 are placed into a first vessel or vein 14. A needle 26 is used to puncture from the vein 14 into an adjacent second vessel or artery 15. An electrode guidewire 16 is inserted through a lumen of the needle 26 into the artery 15. At this point, the needle 26 is removed. It is noted that, while the invention is herein described for a procedural site wherein the first vessel is a vein and the second vessel is an artery, the inventive systems and methods described throughout this application are, of course, applicable to other sites and anatomies suitable for creating an anastomosis between adjacent spaces or conduits, as would be well known by those of skill in the art.

Figure 3:
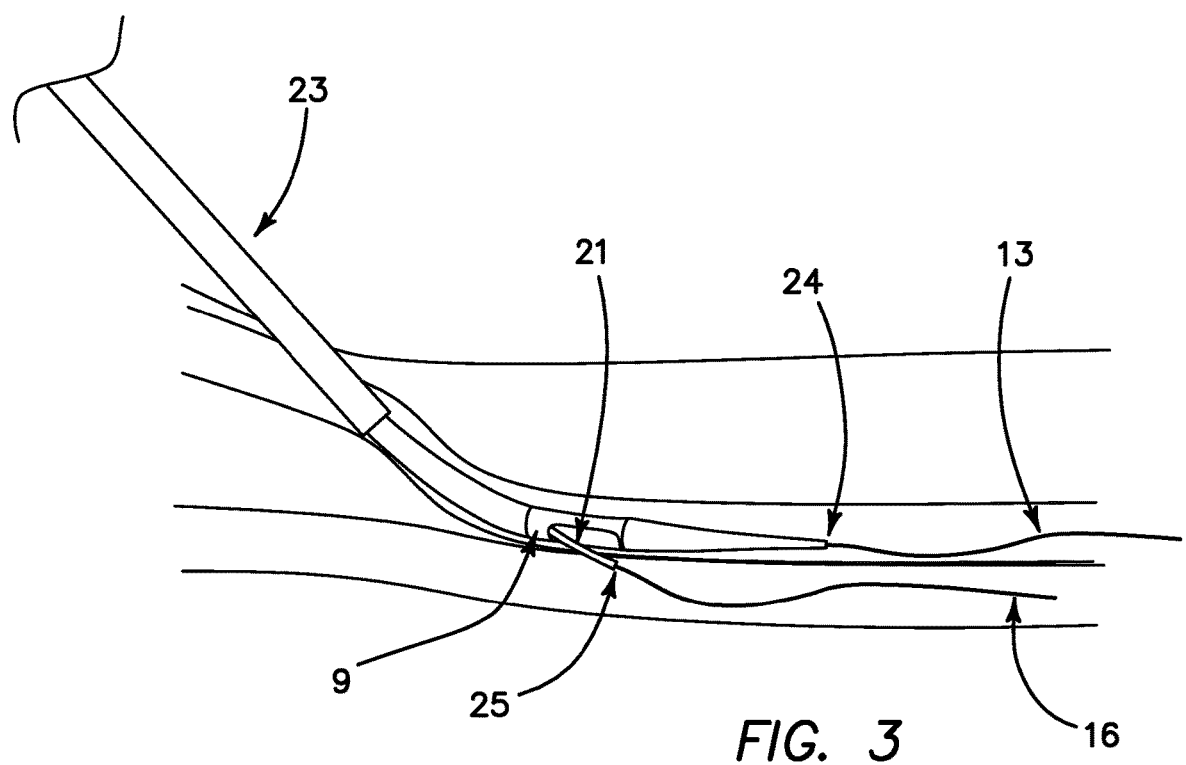
FIG. 3 is a view similar to FIG. 2, wherein the needle has been removed, the main body of the catheter has been advanced over the guidewire into the first vessel, and the electrode has separated from the main catheter body and has entered the lumen of the adjacent vessel.

Referring to FIG. 3, after removal of the needle 26 (FIG. 2), the main body 9 of the catheter 6 is tracked over the venous guidewire 13, which extends through a main body lumen 24, into the vein 14. The electrode guidewire 16 is inserted into an electrode lumen 25. As the catheter is advanced, the electrode 21 separates from the main body 9 and into the arterial lumen 16.

Figure 4:
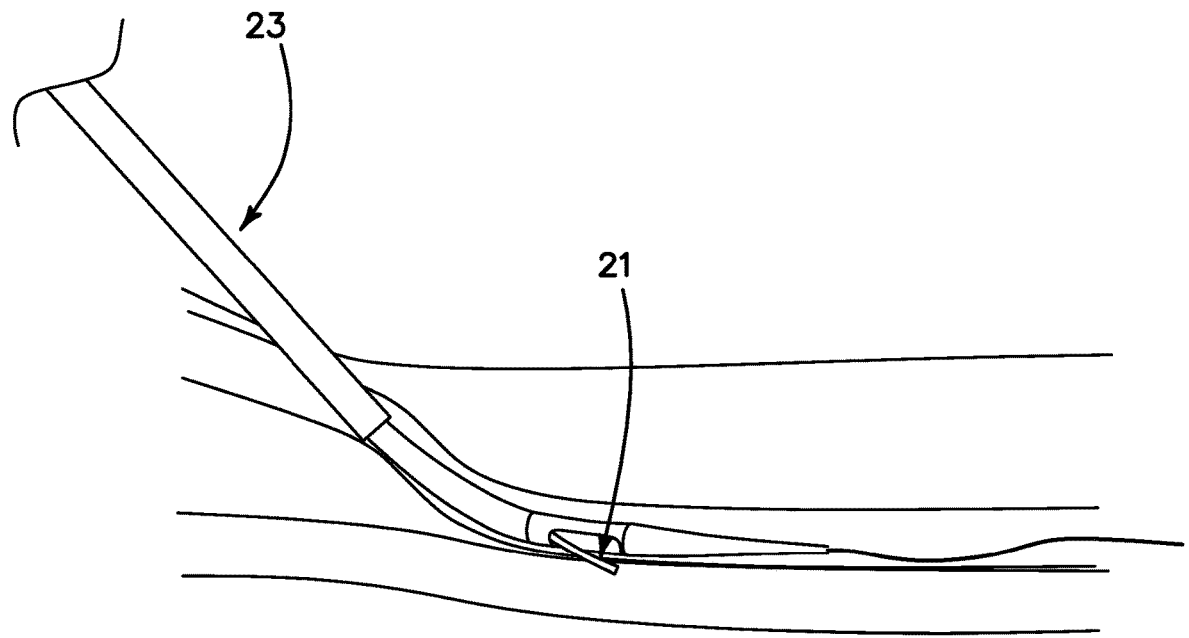
FIG. 4 is a view similar to FIG. 3, wherein the guidewire is retracted, the adjacent sidewalls of the two vessels have been compressed and approximated, and the electrode has been energized and is cutting through the vessel walls.

Now with reference to FIG. 4, next the electrode guidewire 16 is retracted, allowing the spring-loaded electrode 21, because of its resilient bias in the direction of the catheter body, to compress the arterial and venous walls. The electrode 21 is energized and cuts through the vessel walls.

The electrode may be constructed of stainless steel, Nitinol, Nichrome or similar materials. The shape of the electrode may provide the compression of the walls or a tendon wire may be used to pull the electrode against the vessel walls. The electrode 21 may be energized with RF (Radio Frequency), ultrasonic, or resistive heating.

Figure 5:
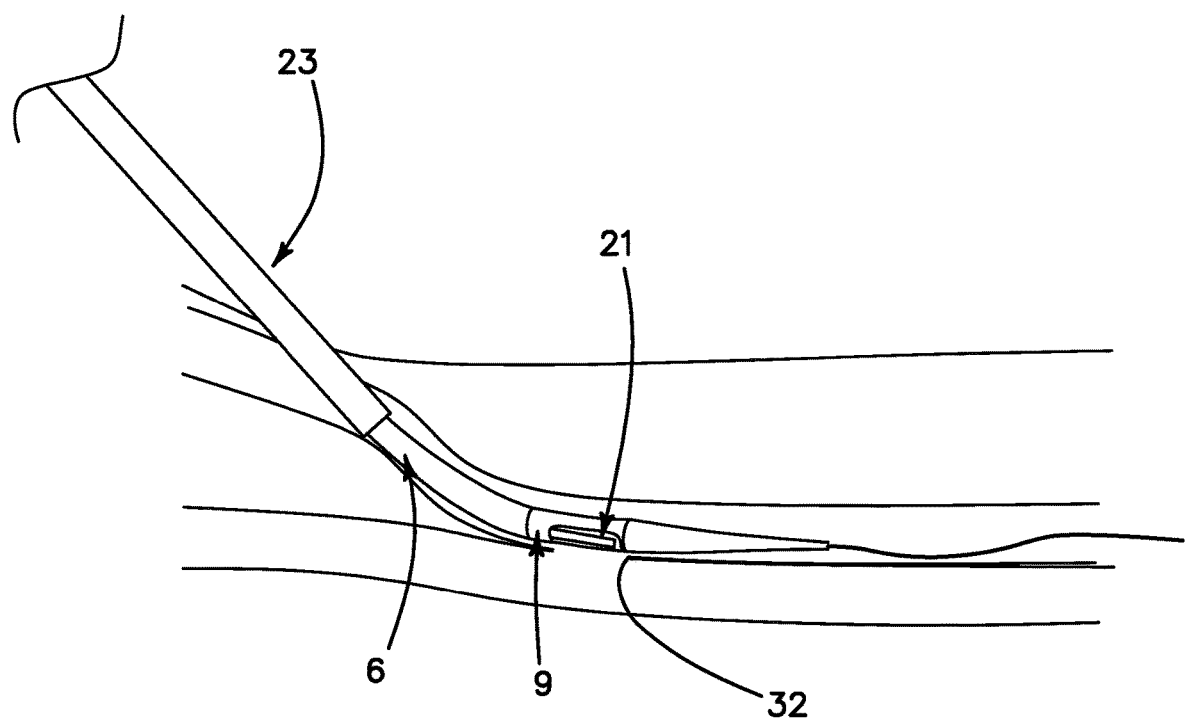
FIG. 5 is a view similar to FIG. 4, wherein the electrode has been retracted to nest within the main catheter body, after an anastomosis between the two vessels has been formed.

As shown in FIG. 5, after activation, the electrode 21 completely nests inside the main body of the catheter 6. The catheter 6 is removed, leaving an anastomosis 32 connecting the vein 14 and the artery 15.

Figure 6:
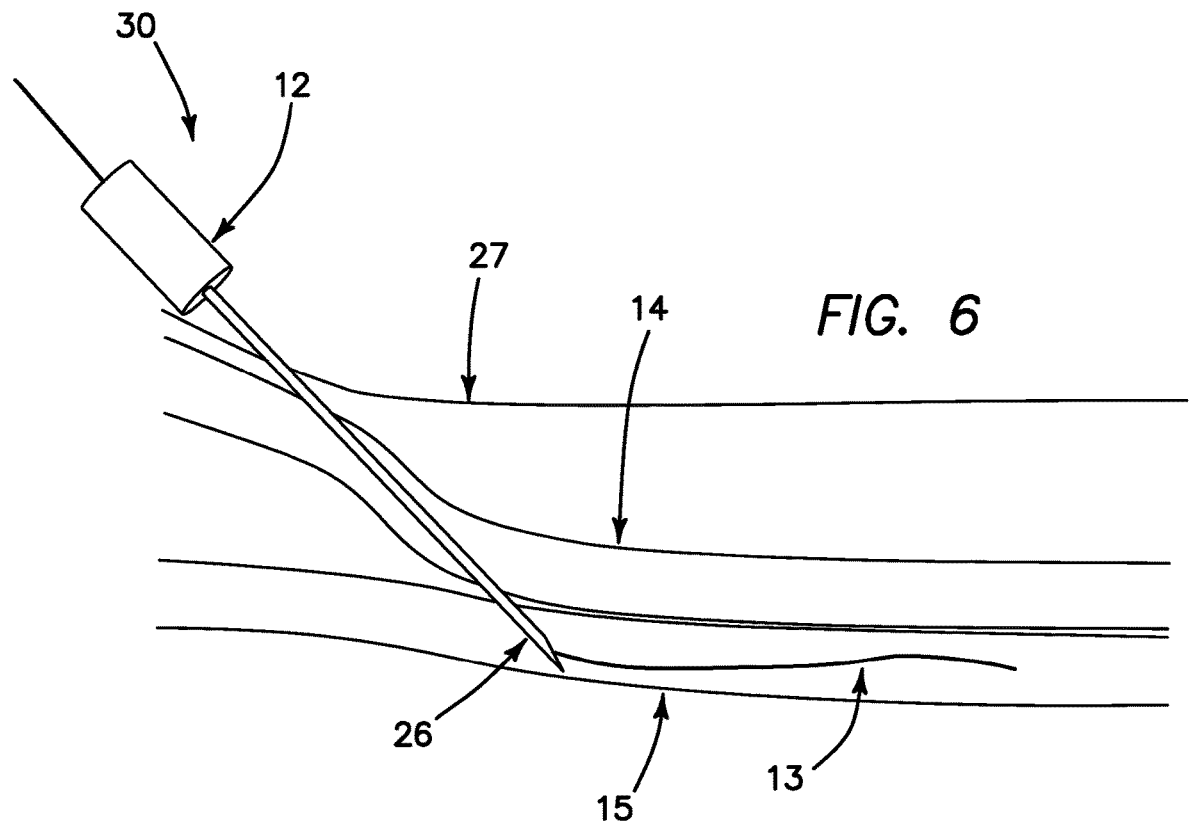
FIG. 6 is a view similar to FIG. 2, illustrating an exemplary modified embodiment of the present invention.

Now, with reference to FIGS. 6-11, a second exemplary embodiment of a resiliently biased cutting electrode 21 is shown. In this embodiment, comprised of a spring-loaded "fixed" electrode, a needle 26 is utilized to puncture the patient's skin 27 and thus gain access to the vein 14, and to puncture into the adjacent artery 15. A 0.014" guidewire 13 is placed through the needle lumen, as illustrated in FIG. 6, into artery 15.

Figure 7:
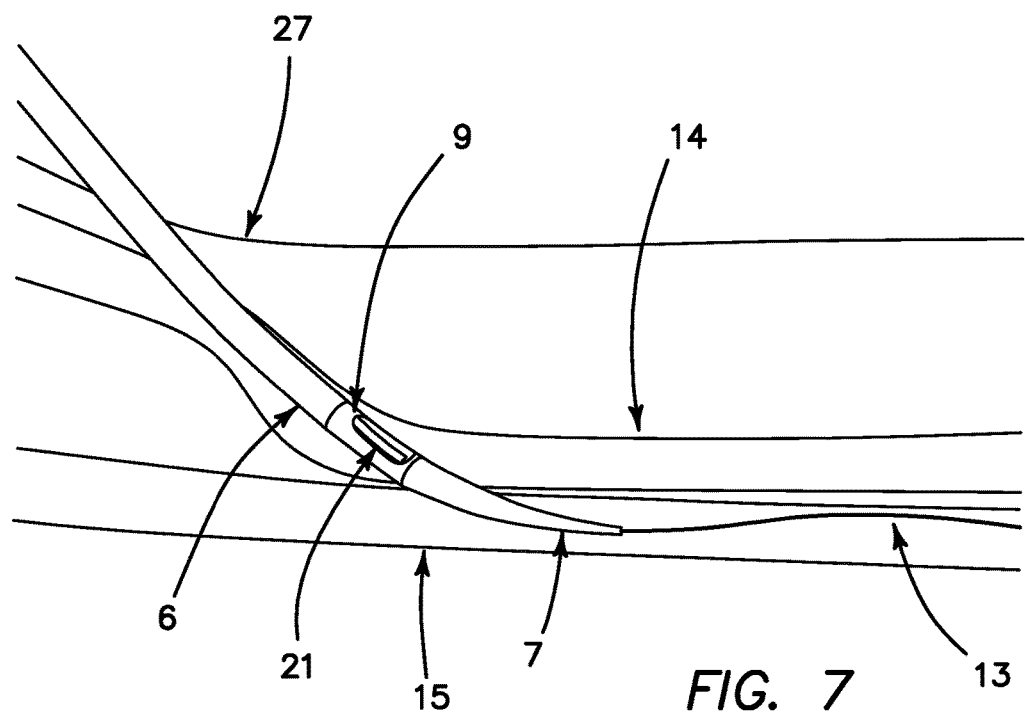
FIG. 7 is a view similar to FIG. 3, illustrating advancement of the modified catheter embodiment to a procedural site.

As shown in FIG. 7, the catheter 6 tracks over the guidewire 13 into the vein 14, and the dilator tip 7 enters the artery 15. The main body 9 and cutting electrode 21 remain in the vein.

Figure 8:
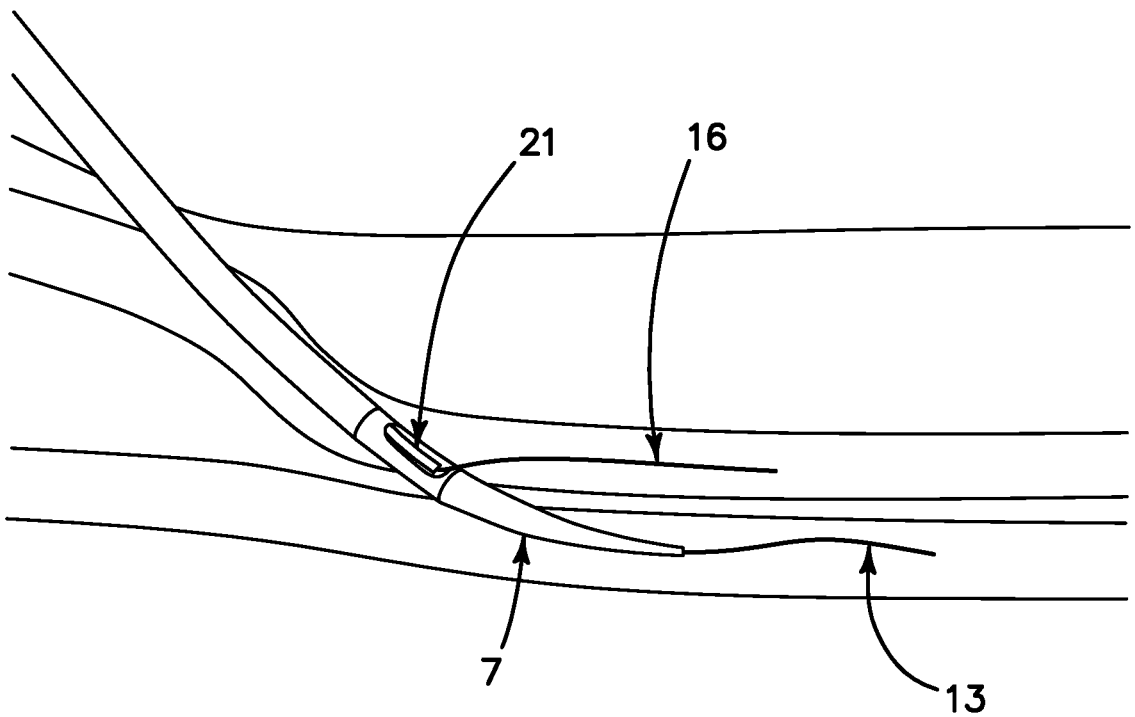
FIG. 8 is a view similar to FIG. 7, wherein an electrode guidewire is extended into the first vessel, through the electrode.
Figure 9:
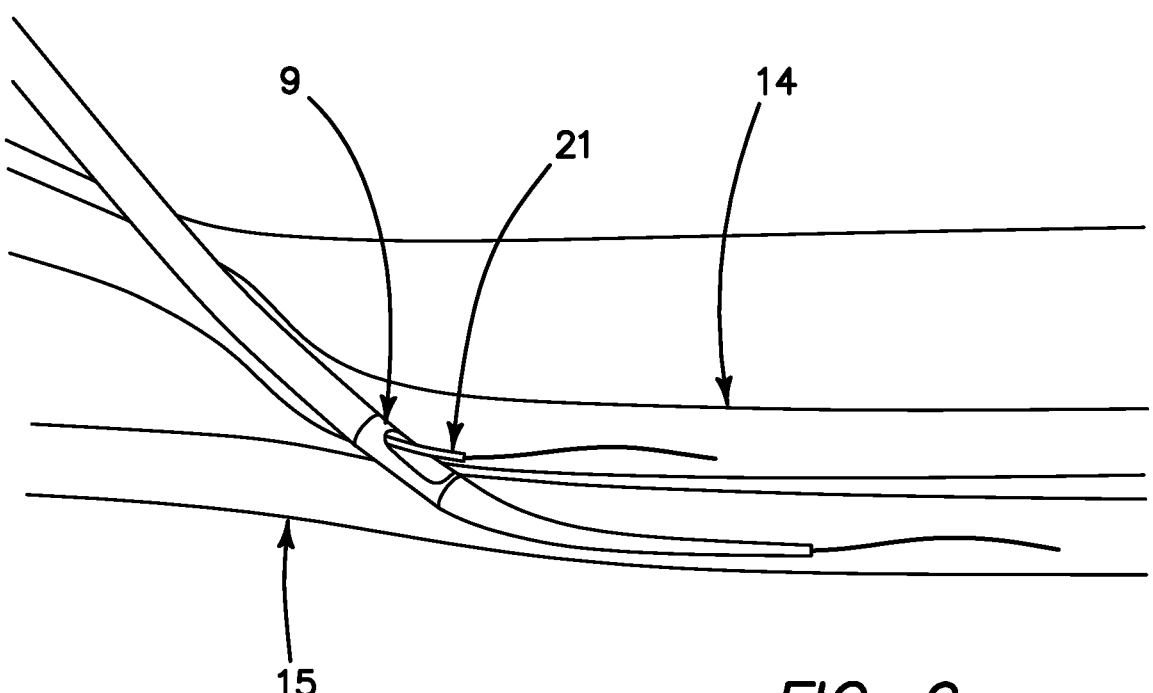
FIG. 9 is a view similar to FIG. 8, wherein the catheter has been advanced distally, lifting the electrode from the catheter main body and compressing and approximating the vessel sidewalls together.

Reviewing, in particular, FIG. 8, it is seen that an electrode guidewire 16 is then placed into the vein 14, through the electrode 21. In FIG. 9, the catheter 6 is advanced forward, lifting the spring-loaded electrode 21 from the main body 9 and functioning to compress the arterial (15) and venous (14) walls together.

Figure 10:
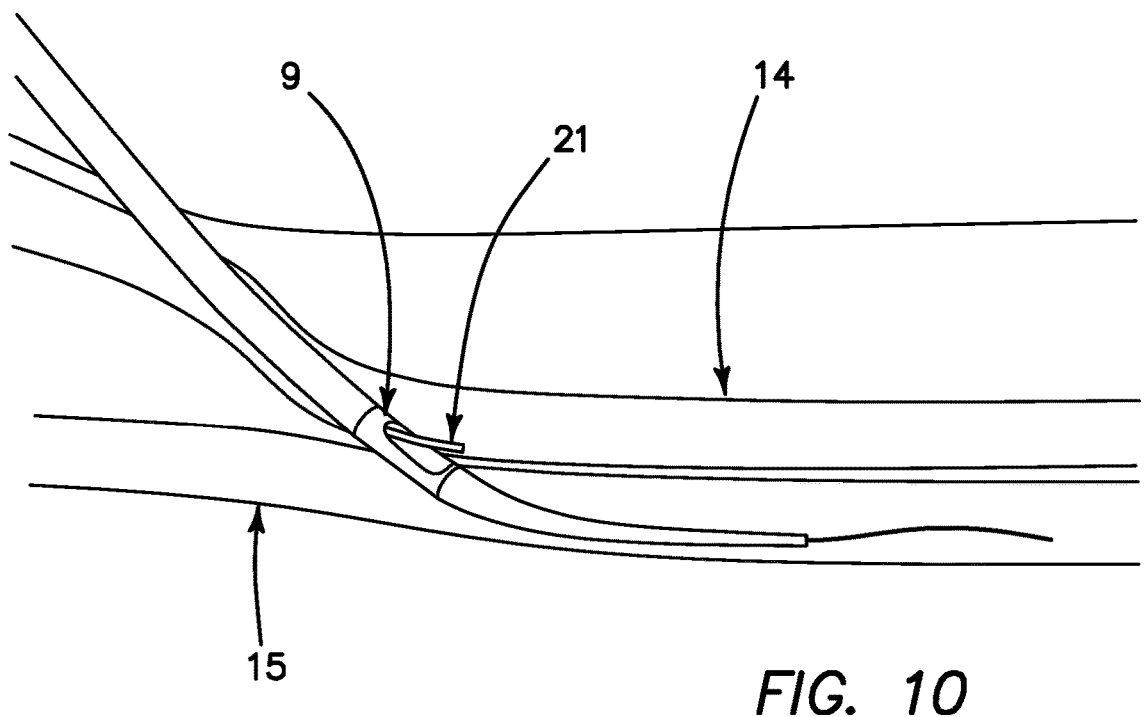
FIG. 10 is a view similar to FIG. 9, wherein the electrode guidewire has been retracted and the electrode energized to cut an anastomosis between the vessels.
Figure 11:
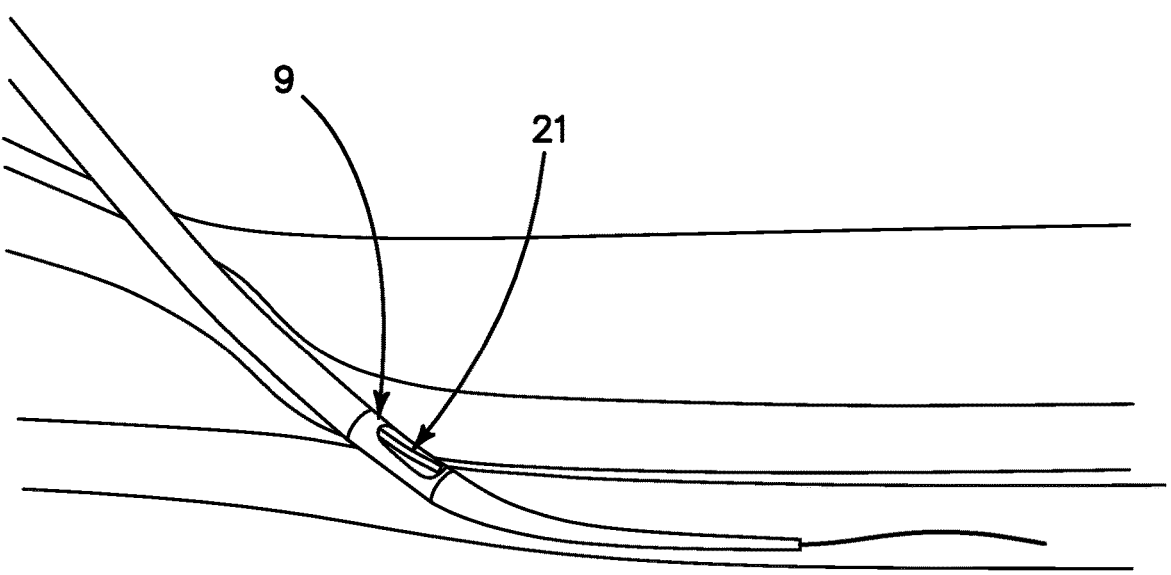
FIG. 11 is a view similar to FIG. 10, wherein the anastomosis has been cut and the electrode is nested inside the main catheter body.

As shown in FIG. 10, the electrode guidewire 16 is then retracted and the spring-loaded electrode 21 compresses the artery 15 and vein 14 against the main body 9 of the catheter. At this point, the electrode 21 is energized using RF, Ultrasonic, or resistive heating technology to cut an anastomosis between the vessels. After energizing, as shown in FIG. 11, the electrode 21 nests inside the main body 9 as the anastomosis is cut between the artery and vein. Once the anastomosis is completed, the device 30 is withdrawn.

Figure 12:
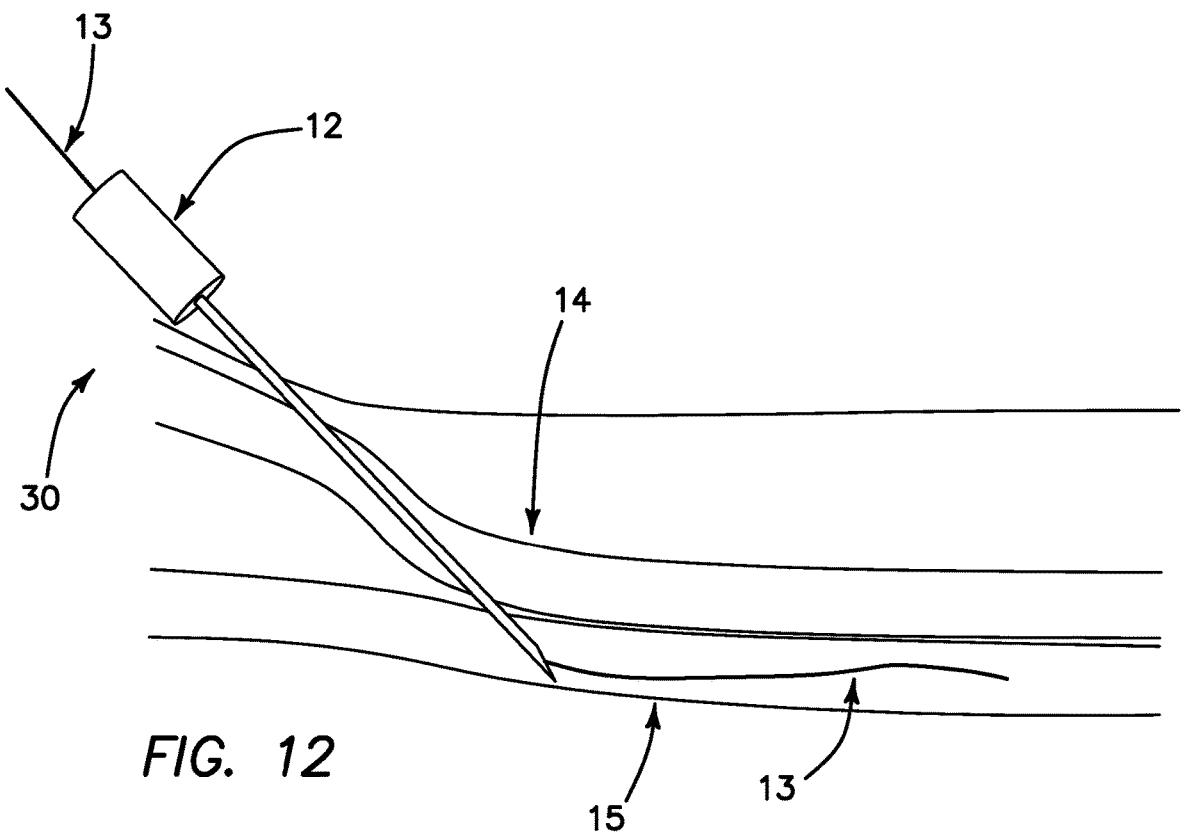
FIG. 12 is a view similar to FIGS. 2 and 6, illustrating still another exemplary embodiment of the present invention.
Figure 13:
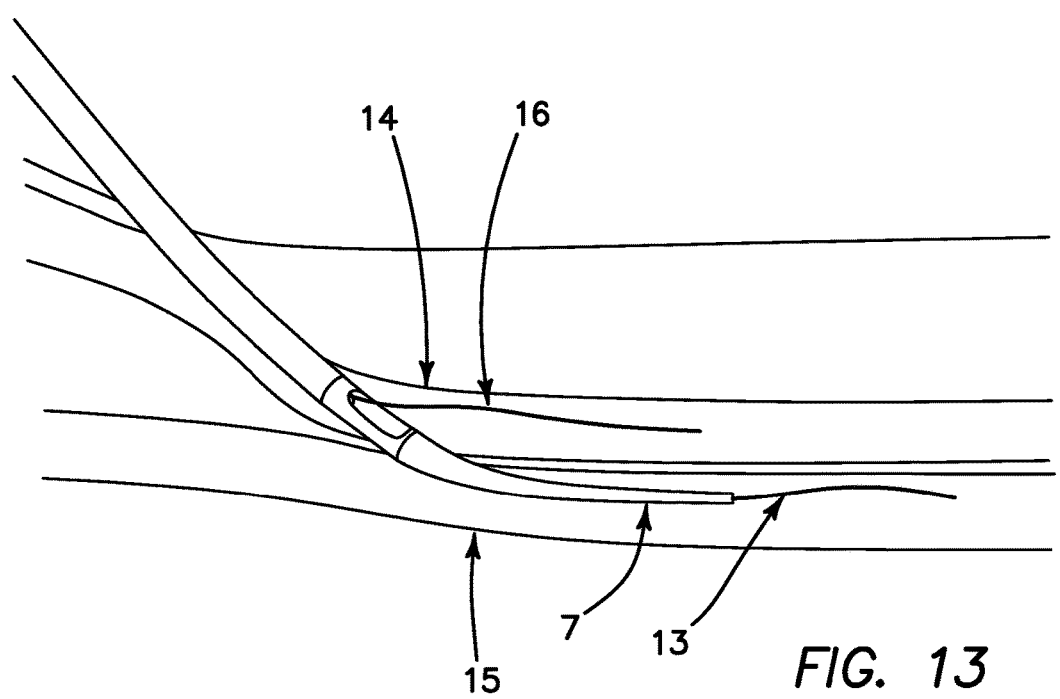
FIG. 13 is a view similar to FIG. 8, illustrating advancement of the modified catheter embodiment and its dilator tip into the adjacent vessel and a guidewire into the first vessel from a side port of the catheter body.

FIGS. 12-17 illustrate a third embodiment of the cutting electrode 21 for performing the inventive procedures discussed herein. In this embodiment and method, a micropuncture needle 12 is used to gain venous (14) access and arterial (15) access, and a guidewire 13 is placed in the artery 15, as shown in FIG. 12. After gaining venous (14) and arterial (15) access, and advancing the dilator tip 7 into the artery 15, a venous electrode guidewire 16 is advanced down the venous catheter 6 lumen and into the vein, as illustrated in FIG. 13.

Figure 14:
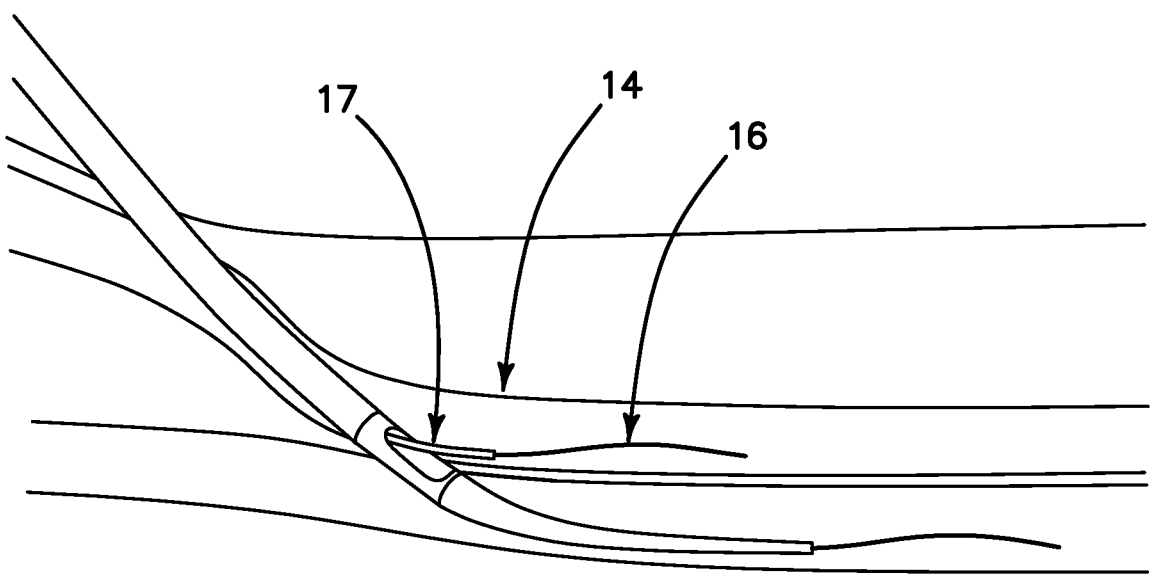
FIG. 14 is a view similar to FIG. 13, wherein a catheter lumen has been extended distally from the catheter side port into the first vessel.
Figure 15:
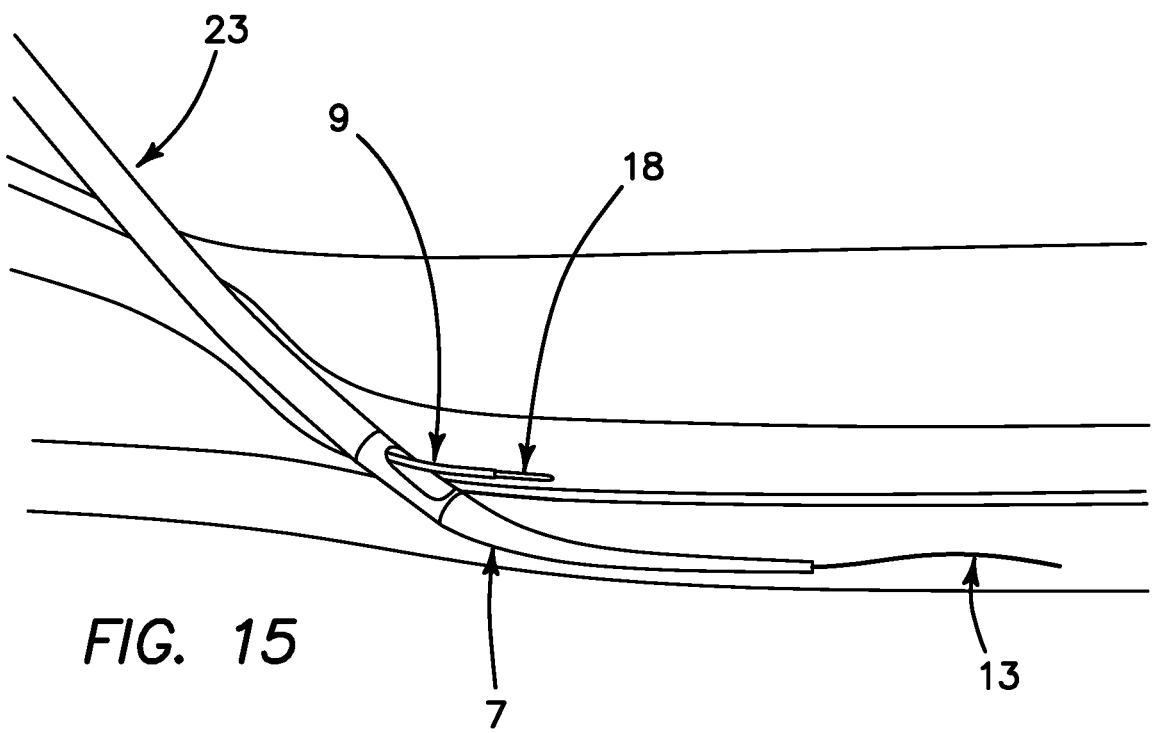
FIG. 15 is a view similar to FIG. 14, wherein the first vessel guidewire has been removed and a cutter wire has been advanced through a first vessel catheter lumen into the first vessel.

Referring to FIG. 14, the thumb tab 3 on the handle 1 is advanced, thereby extending a venous catheter lumen 17 into the vein 14. As depicted in FIG. 15, the venous guidewire 13 is then removed, while a cutter wire 18, preferably formed of a suitable material such as NiTi or stainless steel, is advanced through the venous catheter lumen 17. A molded fitting on the proximal end of the cutter wire 18 is locked into place on the proximal end of the catheter handle 1 to set the cutter wire length.

Figure 16:
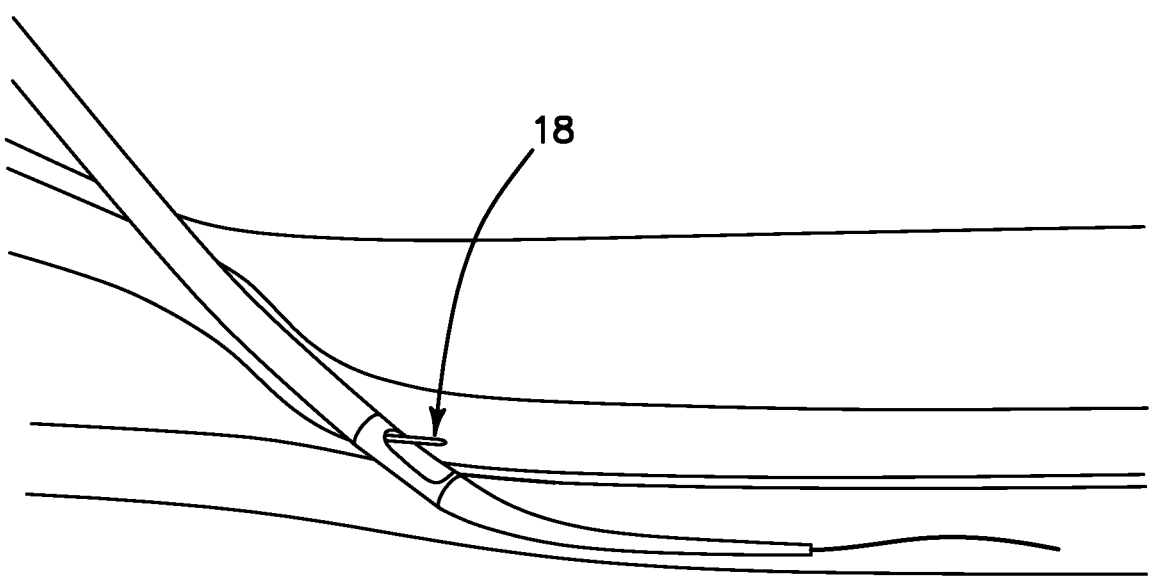
FIG. 16 is a view similar to FIG. 15, wherein the first vessel catheter has been retracted into the main catheter body and the cutter wire has been energized to form an anastomosis.

FIG. 16 illustrates retraction of the venous lumen 17 by retraction of the thumb tab 3. This positions the cutting electrode 18 for fistula creation. Energy (RF, Ultrasonic, or direct heating) is applied to the cutting electrode, after which the cutting electrode cuts a slit, forming the anastomosis. Once the anastomosis is completed, the device 30 is withdrawn.

Figure 17:
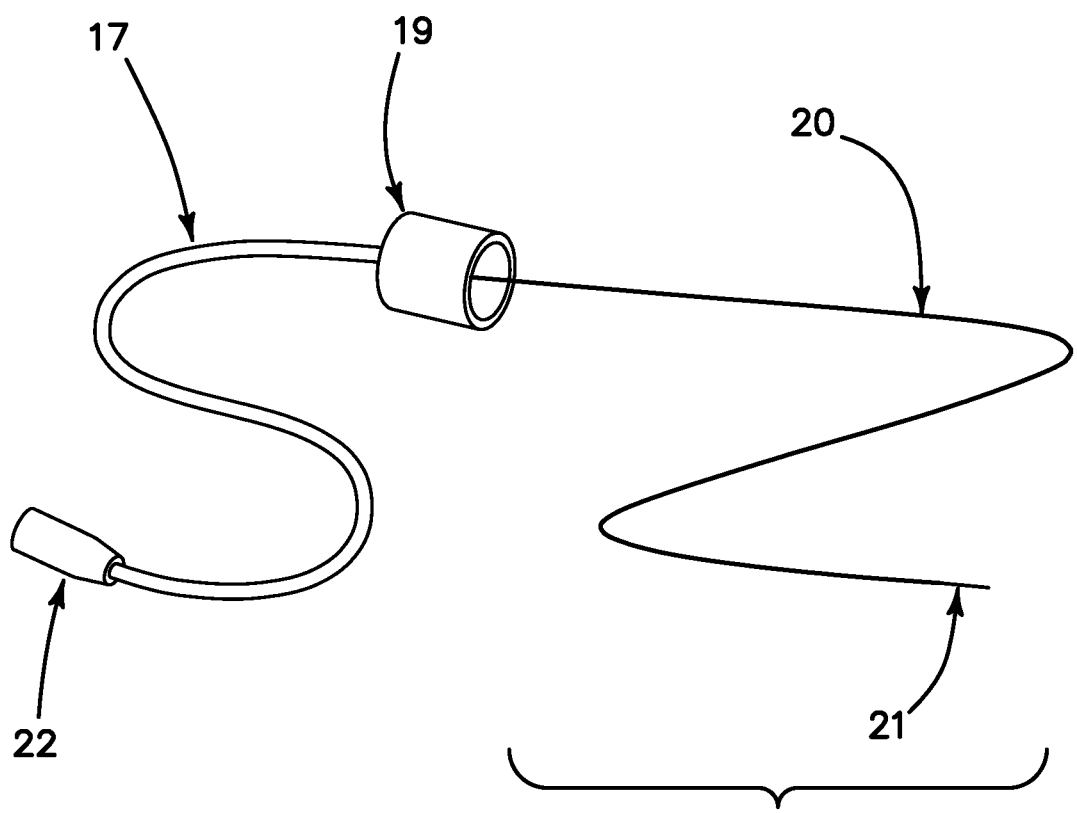
FIG. 17 is a schematic view showing one exemplary approach for retaining and dispensing cutter wire for the embodiment shown in FIGS. 12-16.

FIG. 17 depicts one approach for retaining and dispensing the cutter wire 18 used in this particular exemplary embodiment of FIGS. 12-17. As shown, the cutter wire 18 is comprised of a polyimide insulation 20, or other suitable material, with the cutting electrode 21 disposed at a distal end of the portion 20. The electrode 21 is energized by means of a connector 22 for connection to an energy source, such as an RF power source. A Luer Lock connector 19 may be disposed on an opposed end of the venous lumen 17, from which the cutter wire 18 is extended, and into which it is retracted.

Figure 18:
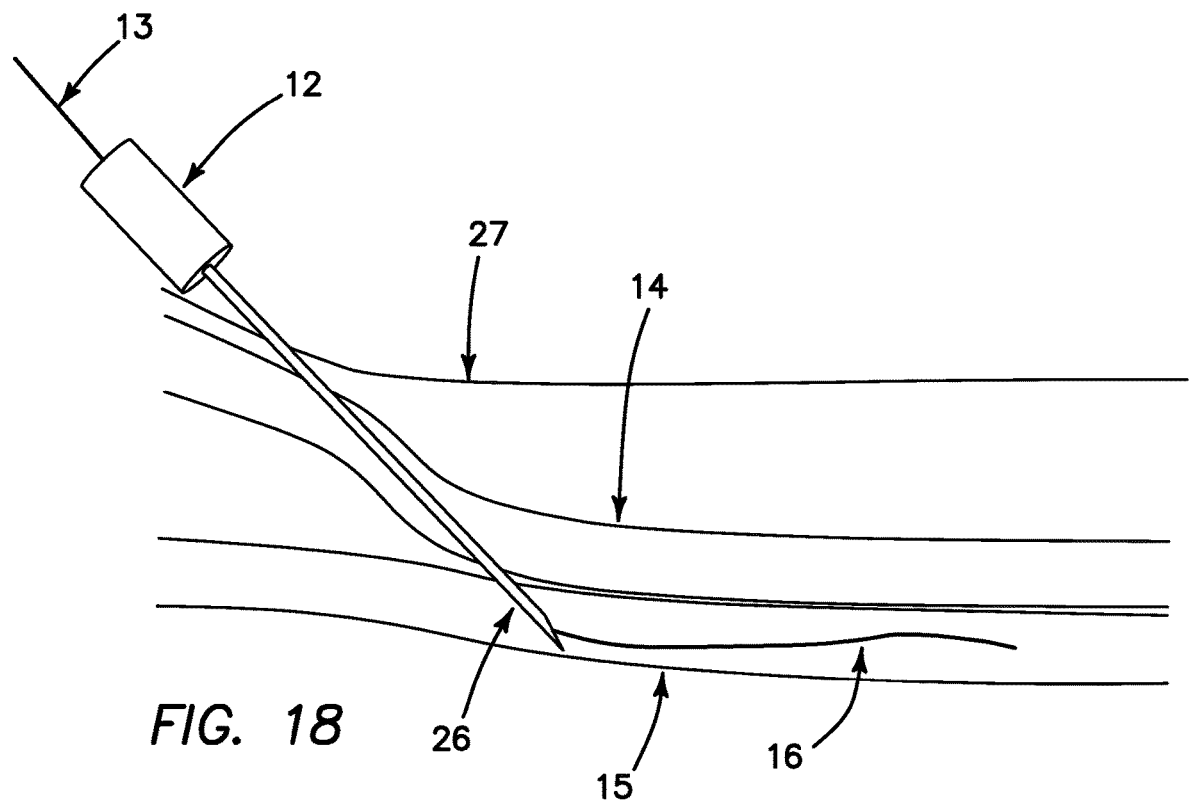
FIG. 18 is a view similar to FIGS. 2, 6, and 12, illustrating yet another exemplary embodiment of the present invention.
Figure 19:
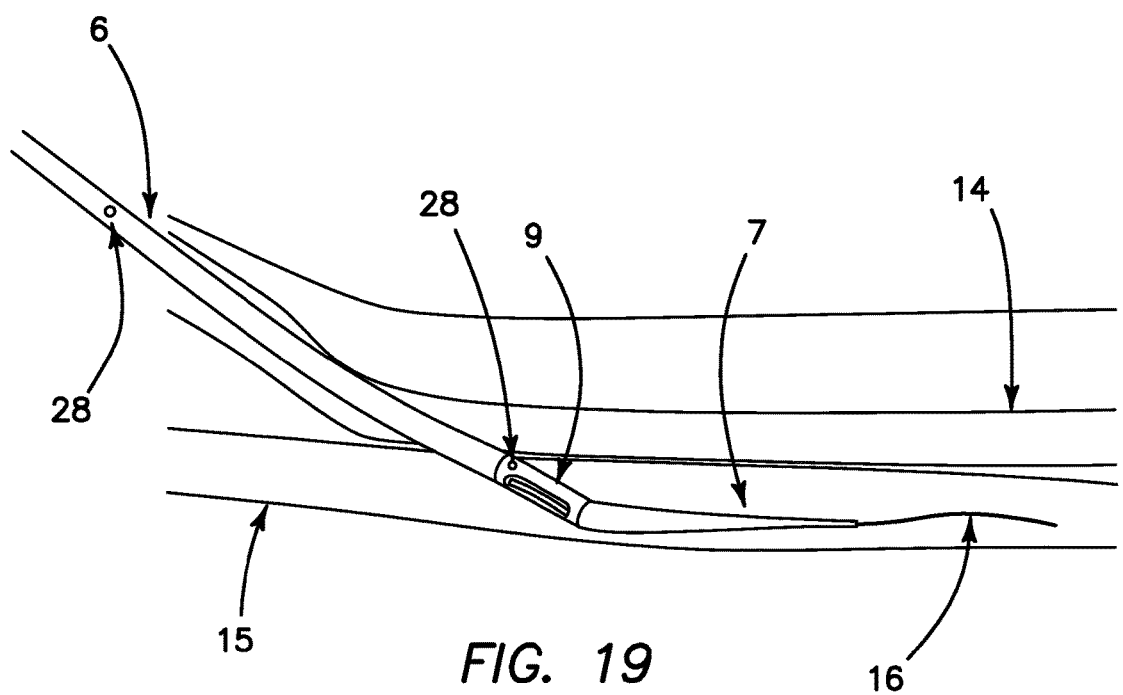
FIG. 19 is a view similar to FIG. 13, wherein a catheter has been tracked over a previously placed guidewire through the first vessel into the adjacent second vessel.

FIGS. 18-22 illustrate yet a fourth exemplary embodiment of the cutting system for the invention. In this embodiment, as shown in FIG. 18, a micropuncture needle 26 is used to puncture the skin 27 and to then gain venous (14) and arterial (15) access. Guidewire 16 is placed in the artery 15 through the lumen of the needle 26. Now, with reference to FIG. 19, the catheter 6 is tracked over the previously placed guidewire 16 through the vein 14 and into the adjacent artery 15, until the main body 9 is disposed in the artery. The dilator tip 7 is smooth and tapered so that it can dilate the skin and vessels without having a sheath in place.

The main body 9 may have a positioning feature 28 in place that detects when the main body has entered the artery, to help position the catheter in the correct location. The positioning feature 28 may be, for example, a pressure sensor, a radiopaque marker, or a bleed port which drips blood out of an external visible port when positioned in the high pressure artery, thereby indicating entry into the artery to the practitioner.

Figure 20:
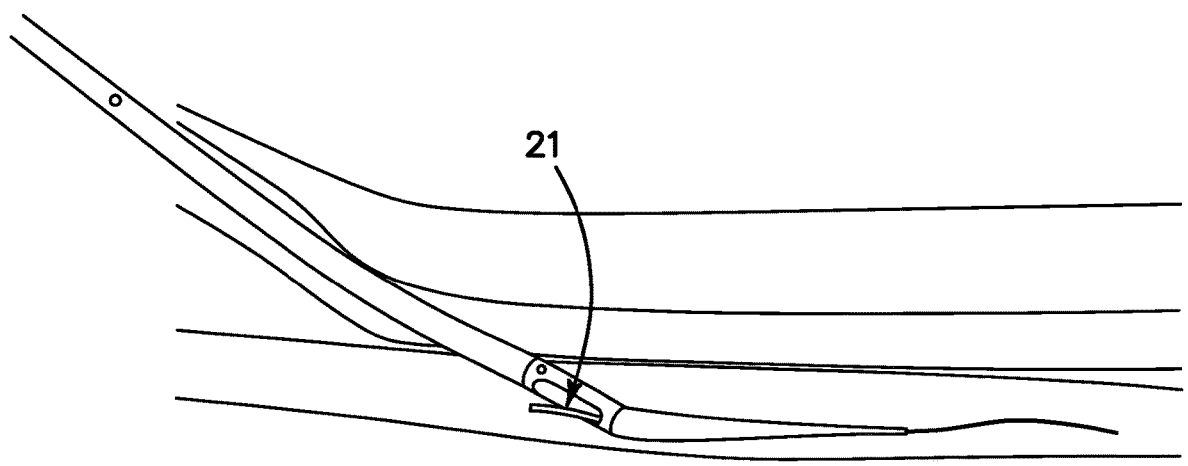
FIG. 20 is a view similar to FIG. 19, wherein a cutting electrode has been deployed in the second vessel.

The electrode 21 may be deployed into the artery 15 via a tendon wire, sliding cam, or other suitable means (FIG. 20).

Figure 21:
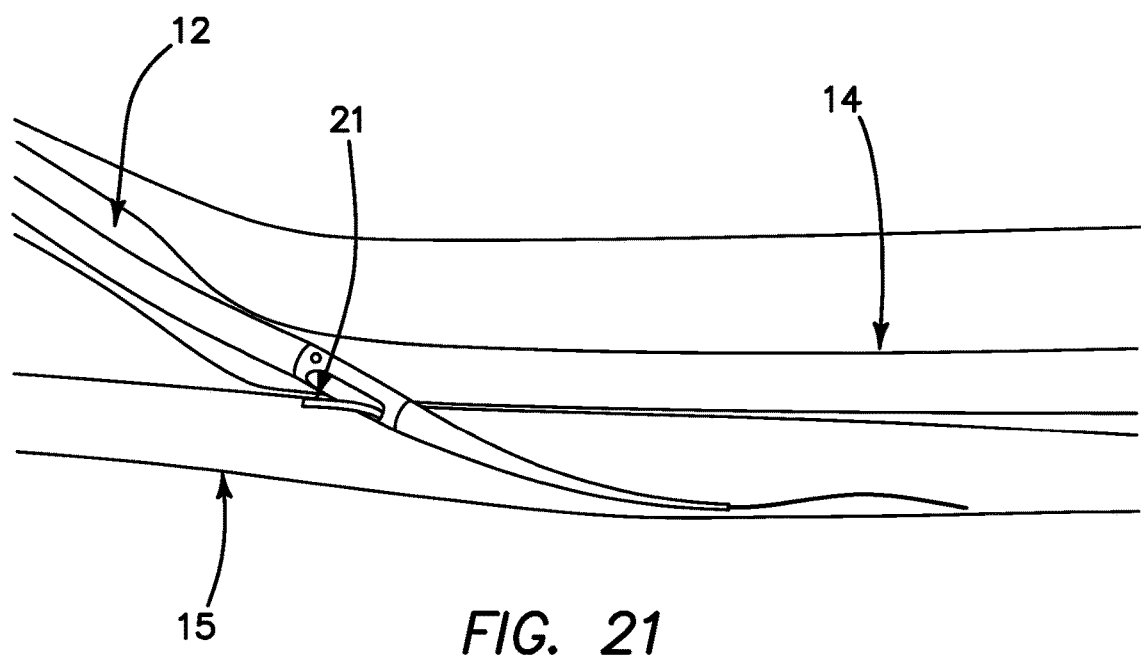
FIG. 21 is a view similar to FIG. 20, wherein the catheter is retracted until the cutting electrode engages and compresses the vessel sidewalls to an approximated position, and the electrode is energized to cut an anastomosis.

Once deployed, the catheter 6 is retracted, as shown in FIG. 21, until the electrode 21 engages and compresses the arterial (15) and venous (14) walls. The electrode 21 is then energized to cut the anastomosis.

Figure 22:
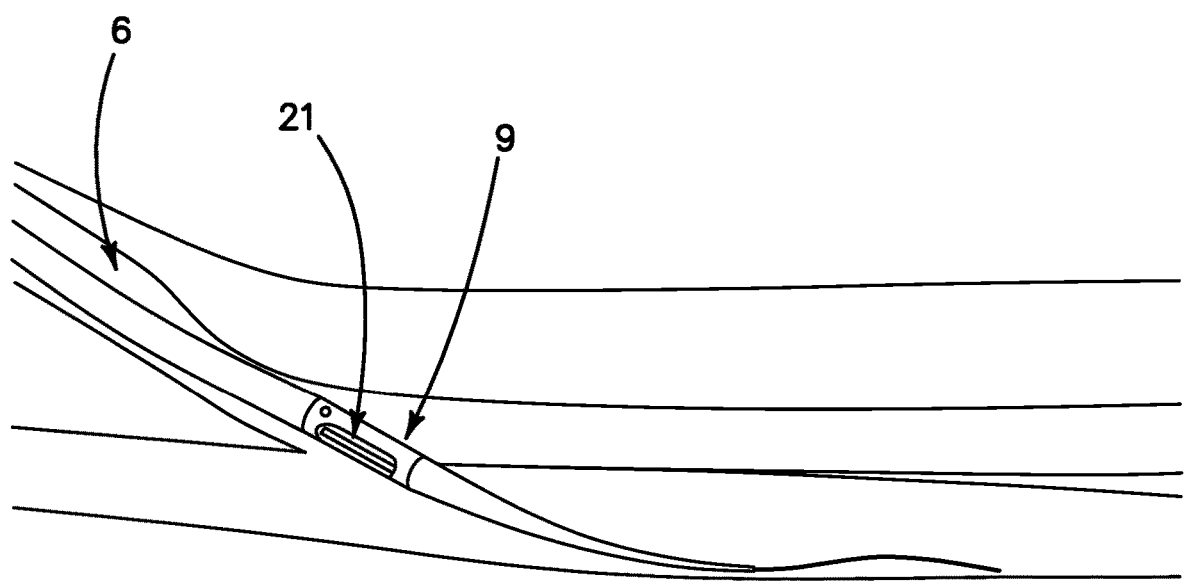
FIG. 22 is a view similar to FIG. 21, wherein the anastomosis has been formed.

When the anastomosis is fully formed, the electrode 21 is retracted to fully nest within the main body 9, as illustrated in FIG. 22, after which the catheter 6 may be readily removed from the procedural site.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A catheter and tissue cutting system for percutaneously creating an anastomosis between a first and second anatomical structure comprising:
   a catheter comprising a main body having a lumen and tapered distal tip, configured to be moved distally into the first anatomical structure over a primary guidewire;
   a cutting electrode, nested in the main body, with a lumen which tracks over a secondary guidewire and is insertable into the second anatomical structure; and
   an energy supply operative to energize the cutting electrode in order to cut a tissue wall of the first anatomical structure;
   wherein the cutting electrode has a resilient bias such that when the cutting electrode is separated from the main body and located in the second anatomical structure, removal of the secondary guidewire causes the cutting electrode to automatically move in a direction of the bias to engage with a tissue wall of the second anatomical structure thereby applying a force to the tissue wall of the second anatomical structure to compress the tissue walls of the first and second anatomical structures.

2. The system as recited in claim 1, and further comprising the primary guidewire extending through and distally from the main body lumen, over which the catheter main body is tracked distally into the first anatomical structure.

3. The system as recited in claim 1, wherein the secondary guidewire extends through and distally from the cutting electrode, over which the cutting electrode separates from the main body into the second anatomical structure.

4. The system as recited in claim 1, wherein the cutting electrode is extendable from and retractable into the main body through a side port in the main body.

5. The system as recited in claim 1, wherein the cutting electrode is comprised of one of stainless steel, Nitinol, or Nichrome.

6. The system as recited in claim 1, wherein the energy supply is configured to supply RF, ultrasonic, or resistive heating energy to the cutting electrode.

7. The system as recited in claim 1, wherein the cutting electrode comprises a cutter wire.

8. The system as recited in claim 7, wherein the cutter wire comprises a polyamide insulation portion and the cutting electrode is disposed at a distal end of the polyamide insulation portion.

9. The system as recited in claim 1, wherein the first anatomical structure is a vein.

10. The system as recited in claim 1, wherein the second anatomical structure is an artery.

11. The system as recited in claim 1, and further comprising a positioning feature on the main body which is configured to detect when the cutting electrode has entered the second anatomical structure.

12. The system as recited in claim 11, wherein the positioning feature comprises one of a pressure sensor, radiopaque marker, or a bleed port.

13. The system as recited in claim 1, further comprising a coaxial piercing member having an inner lumen, the coaxial piercing member configured to be moved distally relative to the main body and to pierce through the tissue wall of the first anatomical structure into the second anatomical structure when the coaxial piercing member is moved over the secondary guidewire placed through the inner lumen of the coaxial piercing member after the main body is inserted into the first anatomical structure over the primary guidewire.

14. The system as recited in claim 13, wherein the piercing member is retractable into the main body lumen.

15. The system as recited in claim 13, wherein the piercing member comprises a micropuncture needle.

* * * * *